(12) United States Patent
Konemann et al.

(10) Patent No.: US 11,181,513 B2
(45) Date of Patent: Nov. 23, 2021

(54) BIOGAS SAMPLING APPARATUS

(71) Applicant: The Board of Regents for Oklahoma State University, Stillwater, OK (US)

(72) Inventors: Charles E. Konemann, Stillwater, OK (US); Bradford M. Kard, Stillwater, OK (US)

(73) Assignee: THE BOARD OF REGENTS FOR OKLAHOMA STATE UNIVERSITY, Stillwater, OK (US)

( * ) Notice: Subject to any disclaimer, the term of this patent is extended or adjusted under 35 U.S.C. 154(b) by 156 days.

(21) Appl. No.: 16/026,504

(22) Filed: Jul. 3, 2018

(65) Prior Publication Data

US 2019/0011411 A1    Jan. 10, 2019

Related U.S. Application Data

(60) Provisional application No. 62/529,626, filed on Jul. 7, 2017.

(51) Int. Cl.
| | |
|---|---|
| *C12M 1/107* | (2006.01) |
| *C12M 1/00* | (2006.01) |
| *C05F 17/90* | (2020.01) |
| *C05F 11/04* | (2018.01) |
| *F17B 1/00* | (2006.01) |
| *F17B 1/02* | (2006.01) |
| *G01N 33/00* | (2006.01) |
| *C02F 11/04* | (2006.01) |
| *A01M 31/00* | (2006.01) |

(52) U.S. Cl.
CPC ............ *G01N 33/004* (2013.01); *C02F 11/04* (2013.01); *C05F 17/90* (2020.01); *C12M 1/107* (2013.01); *C12M 21/04* (2013.01); *C12M 23/36* (2013.01); *G01N 33/0047* (2013.01); *A01M 31/002* (2013.01)

(58) Field of Classification Search
None
See application file for complete search history.

(56) References Cited

U.S. PATENT DOCUMENTS

| | | | |
|---|---|---|---|
| 5,853,247 A * | 12/1998 | Shroyer ................. | B01L 3/505 |
| | | | 383/95 |
| 7,290,669 B1 * | 11/2007 | Hansen .................... | C02F 3/28 |
| | | | 210/525 |
| 7,704,746 B1 * | 4/2010 | White ................. | E21B 41/0064 |
| | | | 436/56 |

(Continued)

*Primary Examiner* — Neil N Turk
(74) *Attorney, Agent, or Firm* — Fellers, Snider, Blankenship, Bailey & Tippens, P.C.; Terry L. Watt

(57) ABSTRACT

There is provided a biogas flux chamber constructed in one embodiment from a metal can with an open bottom and an epoxy interior coating. The chamber is inserted into the soil to allow influx of soil gases. The lid includes a sampling septum and a vent tube to prevent pressure build-up when the lid is in place which allows for an increase in interior gas concentrations. The rubber sampling septum is installed in a hole in the lid. The vent tube is constructed using flexible copper tubing inserted through the lid and secured using a bulkhead-fitting, and rubber O-ring to seal the insertion hole. The copper tubing is bent to form a double-curved 'C' shape which positions the open ends of the tube above and below the lid surfaces.

6 Claims, 3 Drawing Sheets

(56) References Cited

U.S. PATENT DOCUMENTS

| | | | |
|---|---|---|---|
| 2010/0248216 A1* | 9/2010 | Halverson | G01N 1/38 435/5 |
| 2010/0284749 A1* | 11/2010 | Capron | B01D 53/84 405/210 |
| 2015/0329811 A1* | 11/2015 | Chesshire | C12M 21/04 435/167 |

* cited by examiner

BIOGAS SAMPLING APPARATUS

CROSS REFERENCE TO RELATED APPLICATIONS

This application claims the benefit of U.S. Provisional Patent Application Ser. No. 62/529,626 filed on Jul. 7, 2017, and incorporates said provisional application by reference into this document as if fully set out at this point.

TECHNICAL FIELD

This disclosure relates generally to devices for measuring biogas and in more particular, systems and methods of collecting measuring biogas in the field.

BACKGROUND

Production of metabolic gases from many species of mound-building subterranean termites have been well studied in Africa, Australia and South America. However, native North American subterranean termites, *Reticulitermes* spp., metabolic gas emissions have not been well defined in natural settings. This is due in part to termites not being evenly distributed in soil. Carbon dioxide ($CO_2$) and methane ($CH_4$) are produced from multiple sources in the soil, including subterranean termites. Although there have been laboratory studies in this country, what is needed is a method of acquiring biogas measurements in the field where they actually occur.

Guidelines for the construction of flux chambers have been established. They include: 1). The chambers must be fabricated from non-reactive material, such as stainless steel, aluminum, PVC, polypropylene, polyethylene, or Plexiglass®. 2). The materials should be white or coated with a reflective material such as either Mylar® or paint. 3). The chambers should be large enough to cover at least 182 $cm^2$ of the soil surface and have a target height of 15 cm (height can be adjusted lower to increase sensitivity or raised to accommodate plants). 4). The chambers should contain a stainless steel tubing vent tube at least 10-cm long and 6.35 mm in diameter (0.25 inch). 5). The chambers must have a sampling port to enable the removal of gas samples.

The recommended design dictates that a chamber should have two parts: The first part is a permanent anchor (a base) driven into the ground on which the second part, a chamber lid, will tightly fit. There are several methods described in the literature for the collection, storage and analysis of $CO_2$ and $CH_4$ flux measurements, including four basic principles flux chamber design to measure $CO_2$ soil flux. These include closed dynamic chamber systems, closed static chamber systems, open chamber systems, and eddy covariance systems.

In closed dynamic chamber systems, air is circulated between the chamber and the external infra-red gas analyzer (IRGA) with a pump so the $CO_2$ concentration increase is a function of time and is proportional to the $CO_2$ flux. Closed static chambers are of a simpler design, in that they have no provision for mechanical circulation of air. They consist of only the chamber with a sampling port and collar, with samples taken via syringe and analyzed in a laboratory with a gas chromatograph or portable IGRA. Open chambers have a continuous flow of air so that the difference between $CO_2$ concentration entering and exiting the system (gas flow rate) and enclosed soil surface area can be used to calculate fluxes. Eddy covariance systems analyze the exchange rate of $CO_2$ across the interface between the atmosphere and plant canopy by measuring the covariance between fluctuations in vertical wind velocity.

An ability to accurately sample, store and transport intact gas samples from the field to the laboratory is key in assessing gas flux from any source. There are as many ways of sampling, storing, and transporting gas samples as there are chamber methods. As with the different chamber methods, there is no established way of sampling, storage, or transporting gas samples. Unless using a portable gas analyzer such as the LI-6251, syringes and vials are the most common ways of sampling, storage, and transporting.

The importance of protecting the integrity of the sample has also been noted, and the type of syringe and vial utilized can have a significant negative or positive impact on this process. It has been demonstrated that polypropylene syringes can absorb at least 5.8% of gasses into the plastic walls of the syringe and that most syringes lost up to 16% of gas from leakage in 24 h, even with the needle capped with a septum, thus making them unreliable for sample storage.

Glass is non-absorbent and is ideal for gas storage, but if vials are capped with red butyl septa they tend to lose vacuum over time (up to 89% after 136 days) and create contamination in the vial. Grey butyl and silicone septa tend to create less contamination, and the hole created by a needle resealed more efficiently, retaining 98% of the vacuum after 136 days. Others have employed 20 ml plastic syringes that were equipped with three-way valves that prevented leakage or degradation of the gases. In addition, these samples were analyzed within a few minutes of being taken, which also reduced the potential of degradation of the sample. One recommendation is that crimp-top vials with butyl septa be used, but the recommendation stressed the importance of making sure the crimping tool applied adequate, even pressure to ensure an airtight seal. To increase the efficacy of the seal testing, it was recommended that several vials be tested by applying vacuum and evaluating the remaining vacuum one week prior to the next sampling event. The crimping tool could then be adjusted accordingly. The use of a septa system in the design of the chamber can be crucial for gas extraction. In order to calculate the flux from chambers, sampling times must be taken at regular intervals, from time zero minutes to an hour, e.g., 0, 30, 60 minutes, or 0, 20, 40, 60 minutes.

What is needed, then, is an apparatus for collecting biogas in the field that does not suffer from the disadvantages of the prior art.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

There is provided herein an embodiment of a biogas sampling apparatus as is generally illustrated in FIG. 1.

According to one specific embodiment, there is provided a biogas flux chamber constructed from a metal can with an epoxy interior coating to prevent corrosion. The chamber bottom is removed to allow influx of gases emanating from the soil and the lid is modified to include a sampling septum. This allows for interior atmosphere sampling and also accommodates a vent tube to prevent pressure build-up when the lid is in place, while also allowing for increase in interior CO2 and CH4 or other gas concentrations. The sampling septum is installed by punching a hole in the lid and inserting a rubber septum. The vent tube is constructed using flexible copper tubing inserted through the lid and secured using a bulkhead-fitting, and rubber O-ring to seal the insertion hole. The copper tubing is bent to form a double-curved 'C' shape in a manner to allow insertion into the bulkhead fitting and through the rubber O-ring, and also position the open ends of the tube above and below the lid surfaces.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

DETAILED DESCRIPTION

Figure 1:
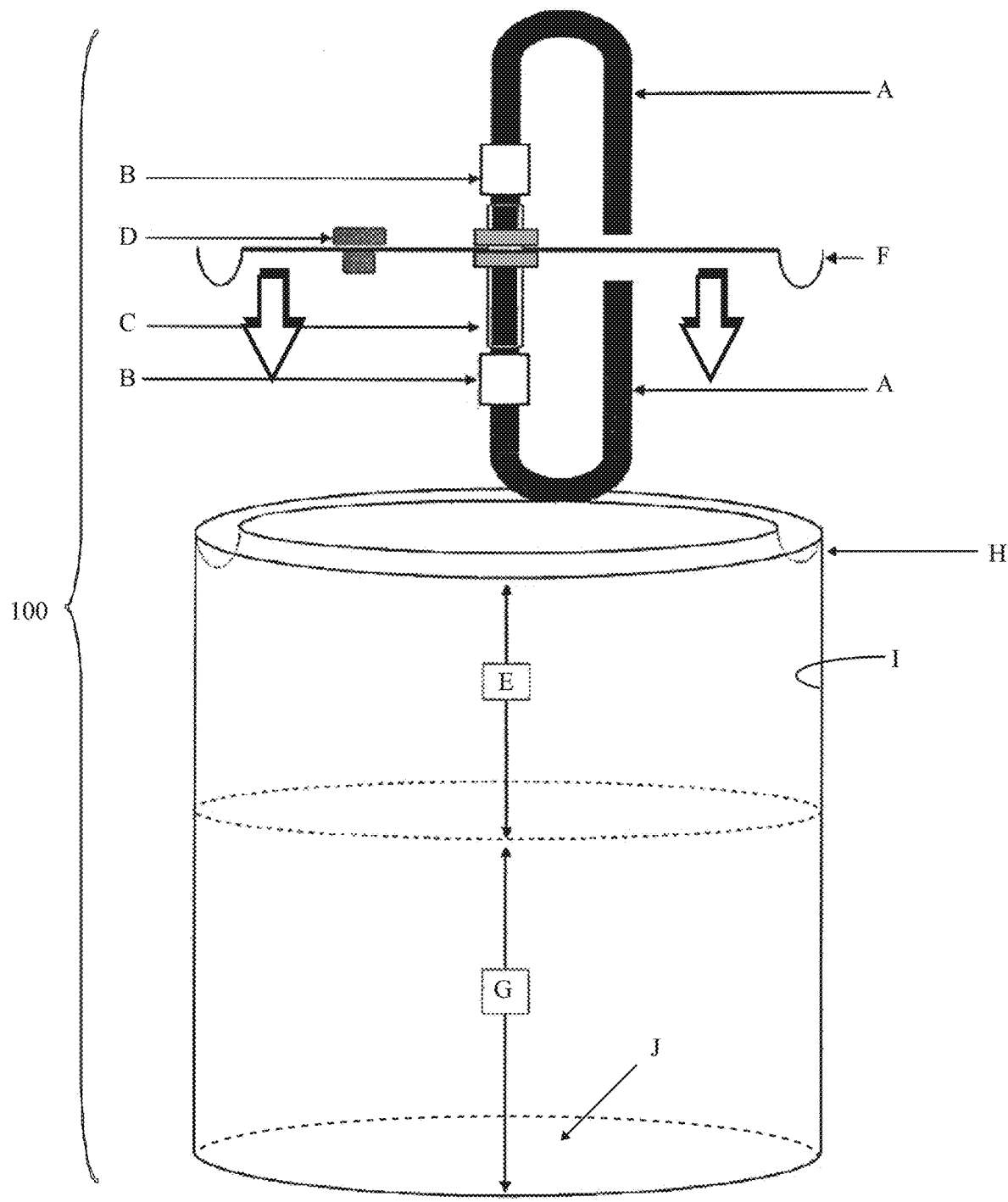
FIG. 1 contains a schematic illustration of an embodiment.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

With respect to FIG. 1, an embodiment of the inventive biogas sampler flux chamber 100 is constructed from a 3.78-L metal paint can H measuring 18.8-cm tall×16.0-cm diameter. In this variation there is an epoxy coating on the interior surfaces I to prevent corrosion. Clearly, any sort of container that is formed from a material that is substantially impermeable to the passage of gas therethrough (e.g., the material might be glass, aluminum, steel, ceramic, certain plastics, etc.) could potentially be used but metal will be preferable in many situations. Additionally, the material chosen should release a gas or vapor that would contaminate the analysis. For purposes of the instant disclosure, the term airtight container will be used to describe a container that is made of a material that is impermeable to the passage of soil gas therethrough and that does not out gas (or that is coated so it does not out gas) in way that would contaminate the soil gas.

Figure 4:
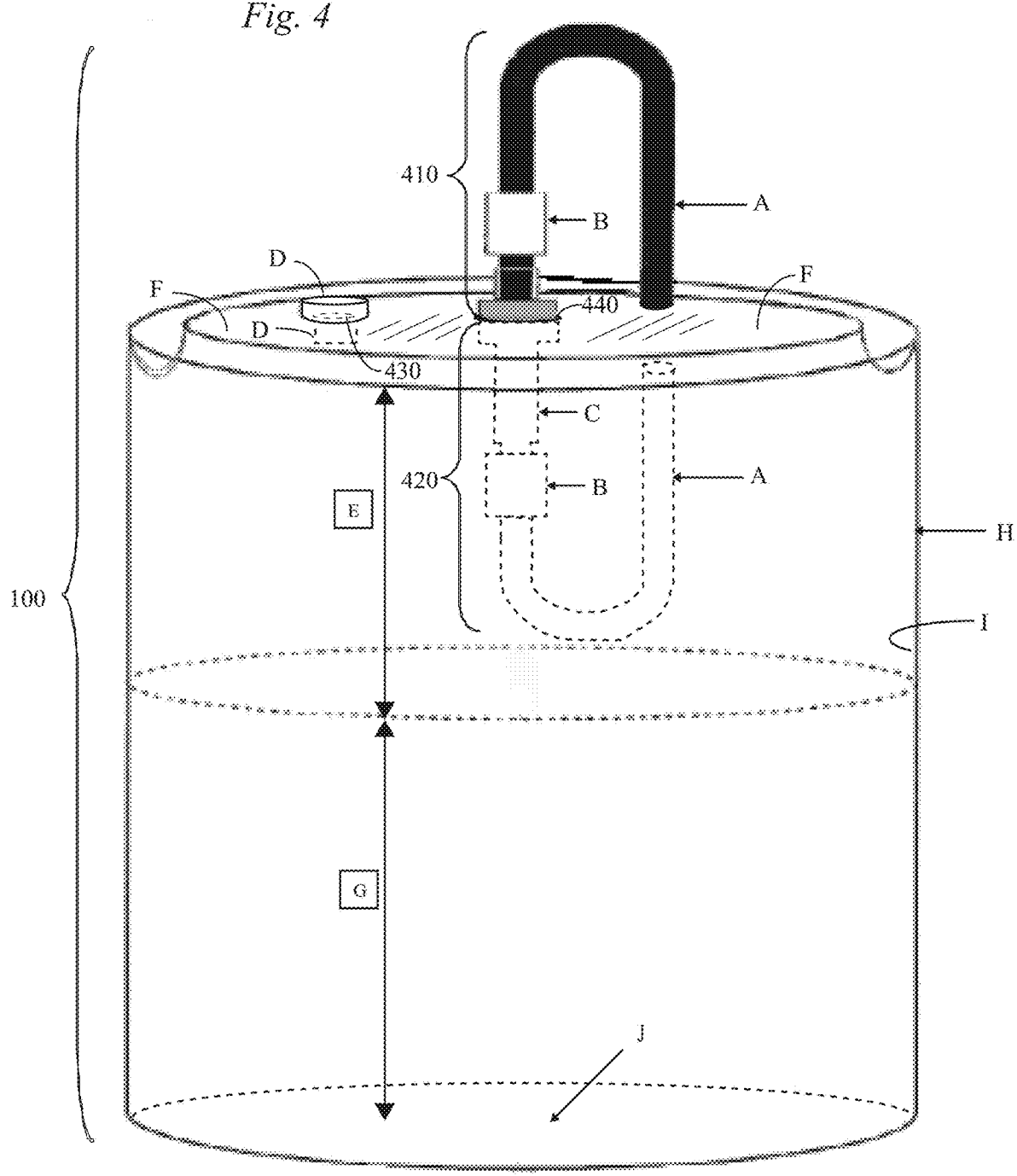
FIG. 4 contains an integrated schematic illustration of the embodiment of FIG. 1.

Chamber bottom J has been removed to allow for influx of gases emanating from the soil. The snap-on lid F was modified to include a sampling septum D. This allows for sampling of the interior atmosphere and also accommodates vent tube A to prevent pressure build-up when the lid is in place. This also allows for an increase in interior $CO_2$, $CH_4$, or other gas concentrations. According to the present example, the sampling septum D was installed by punching a 1.97-cm diameter hole 430 (FIG. 4) in the lid F and inserting a 2.0-cm diameter rubber septum D. The vent tube A is preferably constructed using 0.95-cm outside diameter (0.63-cm inside diameter) flexible copper tubing inserted through the lid and secured using a 0.95-cm-diameter bulkhead-fitting (Part #18088; Midland Metal Mfg.; Kansas City, Mo.), and rubber O-ring (Part #BG50; Midland Metal Mfg.; Kansas City, Mo.) to seal the insertion hole 440 (FIG. 4). Although the vent tube A in the example of FIG. 1 is formed from a single piece of copper tubing, it could also be formed two pieces (e.g., one piece situated outside of the container H 410 and the other in the interior 420) that are placed in fluid communication with each other via standard connection hardware.

Continuing with the present example, the copper tubing A has been cut to 16.0-cm length, then bent to form a double-curved 'C' shape in a manner to allow insertion into the bulkhead fitting and through the rubber O-ring. Preferably, this will also position the open ends of the tube approximately 5-mm above and below the lid F surfaces (FIG. 1). To sample the gases, 20 ml crimp-top vials were used (FIG. 2) along with specialized collection needles of the sort that might be used to draw blood (FIG. 3). In the example of FIG. 1, the letters used there correspond to the following items:

(A) 0.64 cm (X") O. D. copper tubing vent tube 16 cm in length bent to form "U" shape.

(B) 0.952 cm (⅜") compression nut for brass bulkhead union.

(C) 0.64 cm (Y.") Brass bulkhead union with rubber O-rings (2).

(D) Red iso-Butyl septum.

(E) Chamber headspace which is preferably situated 9.3 cm above soil surface.

(F) Snap-on lid.

(G) Wood billets-filled, soil-filled, or other substrate-filled volume.

(H) 3.78-L metal paint can.

(I) Epoxy coating.

(J) Open bottom.

In various embodiments, the base H of the instant sampling device 100 will be inserted into the soil. In some embodiments, the space G might be filled with wood billets, soil, or some other substrate. When wood billets are used, they might generally take the form of strips of wood that are tightly packed and vertically oriented within the space G so as to occupy essentially the entirety of the volume of the interior of the base H. The system 100 is preferably vertically inserted into the soil that is to be sampled so that the base of the chamber H penetrates some distance into the soil. In some cases, the chamber H might be inserted to about one-half of its height into the soil.

In some embodiments, the sampling chamber H might be wrapped in a stainless-steel mesh or other gas permeable barrier so that the open bottom J is covered. That would serve to prevent termites and soil dwelling arthropods, animals and other soil organisms from entering chamber but would allow soil gas to pass through.

Figure 2:
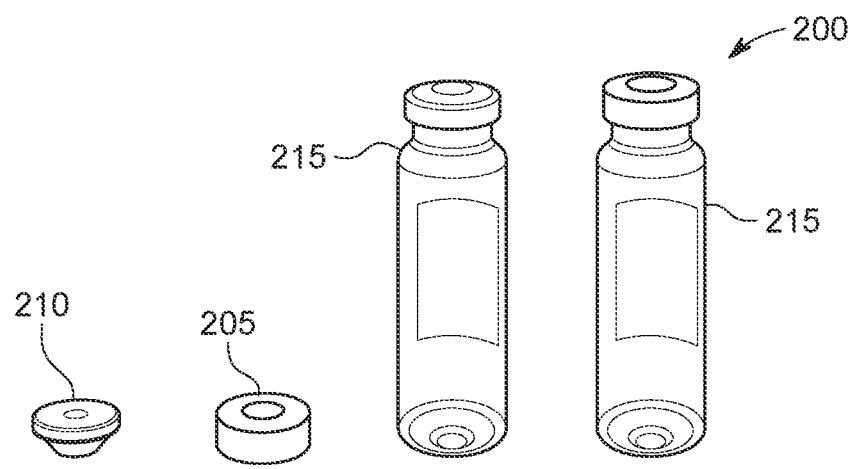
FIG. 2 contains some exemplary gas collection vial assemblies.
Figure 3:
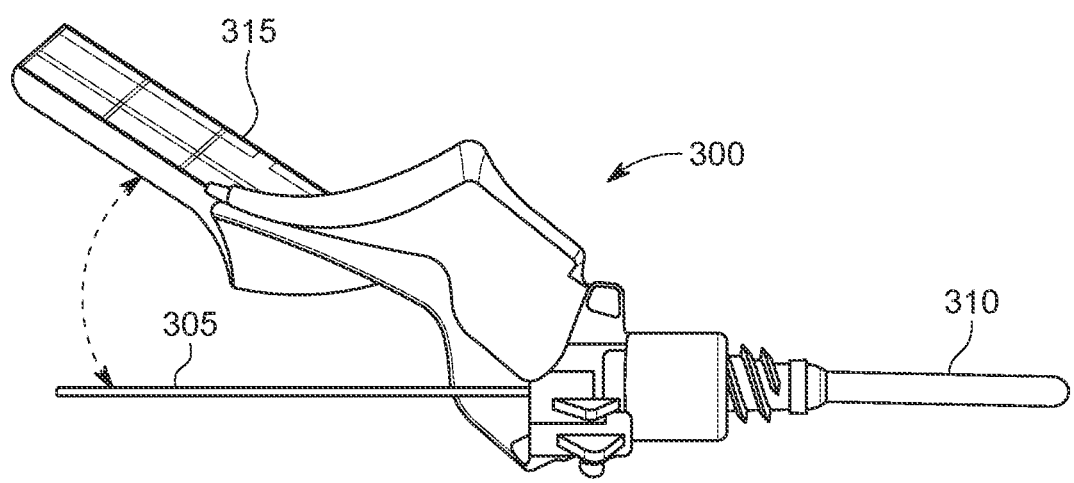
FIG. 3 contains an exemplary gas collection needle.

FIG. 2 illustrates a gas collection vial assembly useful with an embodiment. In this figure is a gas collection vial assembly 200 comprising a 20 ml crimp top vial 215, 20 mm grey butyl septa 205, and 20 mm aluminum crimp ring seal 210. (ThermoFisher Scientific, Rockwood, Tenn., parts #60180-506; #60180-744; #500-334).

FIG. 3 contains an example gas collection needle 300 which is described more fully below. In some embodiments a two-way, dual-point Vacutainer Eclipse blood collection needle might be used. (Daigger Scientific, Vernon Hills, Ill., Product EF2392B).

By way of summary, in the embodiment of FIG. 1, flux chambers H were constructed from 3.78-liter metal paint cans measuring 18.8 cm tall×16.0 cm diameter, with an epoxy coating on the interior surfaces I to prevent corrosion. Chamber bottoms J were removed to allow for influx of gases from the soil. Lids F were modified to include a sampling septum D. This allowed for interior atmosphere sampling and also accommodated vent tube A to prevent pressure build-up when the lid F was in place, while also allowing for increase in interior $CO_2$ and $CH_4$ concentrations.

Continuing with the present example, the sampling septum D was installed by punching a 1.97-cm diameter hole in the lid F and inserting a 2.0-cm diameter rubber septum D. The vent tube A was constructed using 0.95-cm outside diameter (0.63-cm inside diameter) flexible copper tubing that has been inserted through the lid and secured using a 0.95-cm-diameter bulkhead-fitting rubber O-ring to seal the insertion hole. Once it had been cut to 15.2-cm length, the copper tubing was bent to form a double-curved 'C' shape in a manner to allow insertion into the bulkhead fitting and through the rubber O-ring. That also positions the open ends of the tube approximately 5 mm above and below the lid surfaces (FIG. 1).

To minimize the disturbance to the sampled soil, soil monitoring flux chambers will preferably be inserted into the soil by tracing the bottom edge of the cylindrical chamber onto the soil surface and vertically cutting into the soil along the traced edge line with a curved, serrated-edge trowel down to a depth of 7 cm. The chamber can then be inserted into the cut soil by gently tapping on the chamber top edge with a rubber mallet until the chamber bottom edge reach about 7-cm deep. Soil can then be firmly packed against both the interior and exterior walls of the chamber at the soil surface-wall interface to create a tight seal.

Gas Collection. Continuing with the present example, glass vials 200 used for extracting gas samples each consisted of a 20 ml crimp-top vial 215 with a 20 mm grey butyl septa 205 and 20 mm aluminum crimp ring seal 210 (ThermoScientific, Rockwood, Tenn., part #60180-506, #60180-744, and #500-334). The 20 ml vials 200 were prepared as follows. The grey butyl septum 205 was placed on each vial, followed by positioning the aluminum crimp ring seal 210 and fixing it in place on the vial 215 using a manual crimping tool (ThermoScientific, Rockwood, Tenn., part #C4020-100). The atmosphere inside the collection vials was evacuated for 0.30 minutes using a Welch Duo-Seal® vacuum pump (Sargent-Welch Scientific Co., Skokie, Ill. Model #1405).

The vials were used in conjunction with a two-way, dual-point Vacutainer Eclipse blood collection needle apparatus 300 (Daigger Scientific, Vernon Hills, Ill., Product #EF2392B, "dual-point needle apparatus" hereinafter) attached to a modified 50 ml conical centrifuge tube that acted as a holder for the vial. In the example of FIG. 3, the needle safety shield 315 has been pulled back so that the longer/sampling needle 305 can be viewed. In operation, the longer needle 305 of the dual-point needle apparatus 300 is inserted into the flux chamber's septum D, and the shorter needle (not visible), which is covered by a butyl rubber sheath 310 in FIG. 3, can then be inserted into a previously evacuated vial 215 during sample collection to allow gas to be drawn from the interior of the flux chamber H through the dual-point needle apparatus 300 and into the collection vial 215 without the gas sample mixing with the ambient atmosphere. The sheath 310 allows the user to insert the needle contained therein through the septum D and into the flux chamber H without venting the internal chamber gases. The sheath 310 separates to allow the needle to penetrate the vial's rubber septum 210 which allows the vial 215 to draw air from inside the flux chamber H. Then, the sheath 310 reseals when the vial 215 is removed which makes it possible for the dual-point needle apparatus 300 to be reused if that is desired.

Gas Flux Determination.

As an example of how an embodiment might be used in practice, a first group of gas samples was extracted one month after initial field placement of the flux chambers. Flux of gases from all plots were determined by extracting gas samples in sequence at 0-, 30-, and 60-minute timed intervals from each flux chamber.

A Time-0 sample was taken immediately after the lid was placed on the flux chamber, followed by time 30- and 60-minute samples. Crimp-top sampling vials were returned to the lab within 24- to 48-hours, where the air samples were analyzed using a gas chromatograph (GC). Gas samples in the collection vials can be stored for up to five days at 2° C. prior to analysis without degradation of the sample.

Gas Chromatography. Gas samples were analyzed with a Varian®450 GC that incorporated a flame ionization detector (FID) for CH4 analysis, and a thermal-conductivity detector (TCD) for $CO_2$. Gases were separated by an 80/100-mesh-packed column (Mosier et al. 2006; Parkin and Venterea 2010). The GC is interfaced with a Dell OptiPlex desktop computer with Windows XP® Office operating system. Varian's Galaxie® data collection software controls all GC functions including run time, and injector, oven, and detector temperatures. Galaxie software also integrates data and automatically calculates $CO_2$ and $CH_4$ ppm. During analyses, injector temperature was set at 135° C., FID at 300° C., and TCD at 120° C. Samples were analyzed using an isothermal oven temperature program at 50° C. for 7.0-min followed by 1.0-min stabilizing time, totaling 8.0 minutes. A 5.0 ml air sample from each vial was injected into the GC for analysis.

Flux Analyses.

GC analysis provided the area under target peaks for $CO_2$. Dividing the area under the target peak by the area under the standard peak provides a percentage measurement of the target peak in ppm. Data are reported as ppm (mg kg-1). Linear regression determined slope by ppm change over time (0 min; 30 min; 60 min).

With the increased interest in climate change and global warming and the effects of these phenomena on air and soil quality, embodiments of the inventive device provide a straight-forward method and ability to sample air and gas emissions from sailor other substrates. With multiple readings over time, changes in metabolic as well as background non-metabolic gas emissions can be collected and measured. This device could also possibly be used to sample gas emissions in grain storage facilities and silos to detect insect presence, or other animal presence by collecting gases for analyses. Uses of various embodiments of the instant biogas sampler could expand into commercial areas of interest we have not yet anticipated.

Any grain or food storage enclosed facilities could theoretically use the device to sample air and gas emissions for possible detection of dangerous gases or emissions from pest arthropods or invertebrates. Any type of large or small building or storage facility or tunnel could use the device to sample air for any type of gases or contaminants.

Among the advantages of certain embodiments are that they are not complicated to construct and place into use. Inexpensive components are widely available. The inventive device provides a rapid and effective device for gas sampling that is easy to use, transport, ship, and maintain. Can be used in most soil environments, but also can be adapted for use in grain silos or other containers that store materials that the chamber could be inserted into.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)–(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7–91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A biogas flux assembly for collecting biogas samples from the soil or other source, comprising:
   (a) a collector formed of a gas impermeable material, said collector having a cylindrical sidewall, a collector top having a first and second aperture, and an open bottom, said sidewall and said collector top joined together to form a collector interior;
   (b) a perforable septum installed in said first aperture of said collector top, wherein said septum is in fluid communication with said interior of said collector and with an exterior of said collector; and
   (c) a hollow vent tube having a first and a second open terminus, said vent tube passing through said second aperture in said collector top and into said interior of said collector, said first terminus being situated external to said collector and said second terminus being situated within said collector interior, said vent tube providing fluid communication between said collector interior and an ambient atmosphere external to said collector.

2. The biogas flux assembly of claim 1, wherein said collector top is removably joined to said cylindrical sidewall.

3. The biogas flux assembly of claim 1, wherein said vent tube is made of copper.

4. The biogas flux assembly of claim 1, wherein said vent tube comprises:
- (c1) a hollow external vent tube and a hollow internal vent tube joined together at said second aperture,
  - said external vent tube being situated external to said collector and having an open external first terminus and an open external second terminus, said external first terminus being in fluid communication with an atmosphere external to said collector and with said collector interior through said external second terminus opening; and
  - said internal vent tube being situated within said collector interior and having an open internal first terminus and an open internal second terminus, said internal first terminus being in fluid communication with said atmosphere external to said collector through said external vent tube first terminus and in fluid communication with said collector interior through said internal second terminus.

5. An biogas flux assembly for collecting biogas samples from the soil or other source, comprising:
- (a) a collector formed of a gas impermeable material, said collector having a cylindrical sidewall, a collector top having a first and second aperture, and an open bottom, said sidewall and said collector top joined together to form a collector interior;
- (b) a perforable septum installed in said first aperture of said collector top, wherein said septum is in fluid communication with said interior of said collector and with an exterior of said collector;
- (c) a hollow external vent tube and a hollow internal vent tube,
  - said external vent tube having an open first external end and an open second external end, said first external end being attached to said collector top at said second aperture, and said second external end being in communication with an atmosphere external to said collector,
  - said internal vent tube having an open first internal end and an open second internal end, said second internal end being attached to said collector top at said second aperture and in fluid communication with said first external end through said second aperture, said second internal end being in fluid communication with said interior of said collector.

6. The biogas flux assembly of claim 5, wherein said external vent tube and said internal vent tube are made of copper.

* * * * *